United States Patent [19]

Barlics et al.

[11] Patent Number: 4,928,881
[45] Date of Patent: May 29, 1990

[54] AIR FRESHENER

[75] Inventors: John J. Barlics, North Edison; Glen D. Barlics, South Plainfield, both of N.J.

[73] Assignee: Inman Mold Manufacturing Co., Inc., Rahway, N.J.

[21] Appl. No.: 176,792

[22] Filed: Apr. 1, 1988

[51] Int. Cl.$^5$ .............................................. A61L 9/08
[52] U.S. Cl. ...................................... 239/44; 239/289
[58] Field of Search ................... 239/44, 47, 6, 45, 46, 239/289; 220/302, 306

[56] References Cited

U.S. PATENT DOCUMENTS

| | | |
|---|---|---|
| D. 130,228 | 11/1941 | McCartney . |
| D. 130,560 | 12/1941 | Lowenstein . |
| D. 148,766 | 2/1948 | Cobbs . |
| D. 208,421 | 8/1967 | Frazier . |
| D. 250,542 | 12/1978 | Murakami . |
| D. 252,102 | 6/1979 | Mandon et al. . |
| D. 289,678 | 5/1987 | Kwiatkowski . |
| D. 289,920 | 5/1987 | O'Neil, Jr. . |
| D. 293,366 | 12/1987 | O'Neil, Jr. . |
| D. 295,675 | 5/1988 | Demarest . |
| 1,644,482 | 10/1927 | Muller ................................ 239/47 |
| 2,234,903 | 3/1941 | Muench . |
| 2,997,282 | 8/1961 | Binter et al. .................... 239/51.5 X |
| 3,041,031 | 6/1962 | Pearson . |
| 3,724,756 | 4/1973 | Maltenfort ....................... 239/44 X |
| 3,861,991 | 1/1975 | Kim ................................. 239/44 X |
| 3,908,906 | 9/1975 | Crowle et al. . |
| 3,935,944 | 2/1976 | Wilson et al. . |
| 3,990,848 | 11/1976 | Corris . |
| 4,090,636 | 5/1978 | Norton ............................ 220/307 |
| 4,210,258 | 7/1980 | Von Holdt ...................... 220/306 |
| 4,261,461 | 4/1981 | Kizlauskas . |
| 4,452,382 | 6/1984 | Von Holdt ..................... 220/307 X |
| 4,605,165 | 8/1986 | Van Loveren et al. ............ 239/6 |
| 4,739,928 | 4/1988 | Oried ................................ 239/45 |
| 4,742,960 | 5/1988 | Bustillo et al. .................... 239/47 |

FOREIGN PATENT DOCUMENTS

| | | | |
|---|---|---|---|
| 522993 | 3/1958 | Canada ............................ 239/44 |
| 858334 | 12/1976 | Canada ........................... 220/307 |
| 1500405 | 11/1967 | France . |

Primary Examiner—Andres Kashnikow
Assistant Examiner—Kevin P. Weldon
Attorney, Agent, or Firm—Ralph W. Selitto, Jr.

[57] ABSTRACT

Disclosed herein is an air freshener of the type which releases a fragrance by permitting a scent-producing liquid to be evaporatively diffused into the surrounding atmosphere. A wick-like member, which is made from a material capable of conveying the scent-producing liquid by capillary action, is employed for the purpose of conveying the scent-producing liquid from a source located internally of the air freshener to a liquid-diffusing site located on an external surface of the air freshener. The wick-like member extends in a continuous manner from the source of the scent-producing liqud to the liquid-diffusing site, whereby the scent-producing liquid is diffused to the atmosphere directly from the wick-like member itself. A circumferentially continuous spring-like member forms an internal liquid-tight seal in order to inhibit the inadvertent leakage of the scent-producing liquid from the air freshener. The wick-like member is maintained in a holder adapted for removable insertion into an open upper end of a base of the air freshener. By removing the wick-like member and the holder from the base, the base may be used as a receptacle for something other than the scent-producing liquid.

15 Claims, 2 Drawing Sheets

AIR FRESHENER

FIELD OF THE INVENTION

The present invention relates to air fresheners, and, more particularly, to air fresheners of the liquid variety (i.e., air fresheners which release a fragrance by permitting a scent-producing liquid to be diffused into the surrounding atmosphere by the process of evaporation).

BACKGROUND OF THE INVENTION

Liquid-type air fresheners have been commercially available for many years. One such air freshener includes a lower portion, which contains a scent-producing liquid, and an upper portion, which holds a scent pad. A wick, which is made from material different from that of the scent pad, conveys the scent-producing liquid to the scent pad by capillary action. Because the scent pad and the wick are separate and autonomous elements, it is difficult to maintain them in the intimate contact required to achieve the proper transfer of the scent-producing liquid from the wick to the scent pad. If the scent-producing liquid is not properly transferred from the wick to the scent pad, the diffusion of the liquid into the surrounding atmosphere will be impaired, thereby adversely affecting the operation of the air freshener.

The operation of this prior art air freshener is also adversely affected by its use of the scent pad, which functions like a filter and therefore is susceptible to clogging. If the scent pad becomes clogged, it will no longer diffuse the scent-producing liquid into the surrounding atmosphere at a constant and uniform rate.

Another disadvantage of this prior art air freshener is its susceptibility to leakage due to the threaded connection which exists between an external surface of its lower portion and an internal surface of its upper portion. The use of a threaded connection is also disadvantageous because it increases production costs and complicates the assembly process.

SUMMARY OF THE INVENTION

The present invention relates to a new and improved air freshener which includes a base adapted to contain scent-producing liquid and a conveying mechanism adapted to convey the scent-producing liquid to a liquid-diffusing site from which the scent-producing liquid can be evaporatively diffused into the surrounding atmosphere. In accordance with one aspect of the present invention, the conveying mechanism is a wick-like member made from a material capable of conveying the scent-producing liquid from the base to the liquid-diffusing site by capillary action. The wick-like member extends in a continuous manner from the base to the liquid-diffusing site, thereby avoiding the use of a separate scent pad. Because the scent-producing liquid is diffused directly from the wick-like member rather than from a separate scent pad or similar device, the present invention promotes the diffusion of the scent-producing liquid at a relatively constant and uniform rate.

In accordance with another aspect of the present invention, a spring-like member is employed to seal, in a liquid-tight manner, an internal joint formed between the base and a holder mounted within the base and adapted to maintain one end of the wick-like member at the liquid-diffusing site. The spring-like member has an elasticity selected such that the spring-like member is constantly and automatically urged against the surrounding base, whereby the inadvertent leakage of the scent-producing liquid from the base is inhibited.

In accordance with a still further aspect of the present invention, the wick-like member and its associated holder are removably supported in an open upper end of the base. Thus, the wick-like member and the holder can be removed from the base so that the base may be used as a receptacle for something other than the scent-producing liquid. For example, with the wick-like member and the holder removed, the base may be filled with potting soil and used as a planter.

BRIEF DESCRIPTION OF THE DRAWINGS

For a better understanding of the present invention, reference is made to the following detailed description of an exemplary embodiment thereof considered in conjunction with the accompanying drawings, in which.

DESCRIPTION OF THE EXEMPLARY EMBODIMENT

Figure 1:
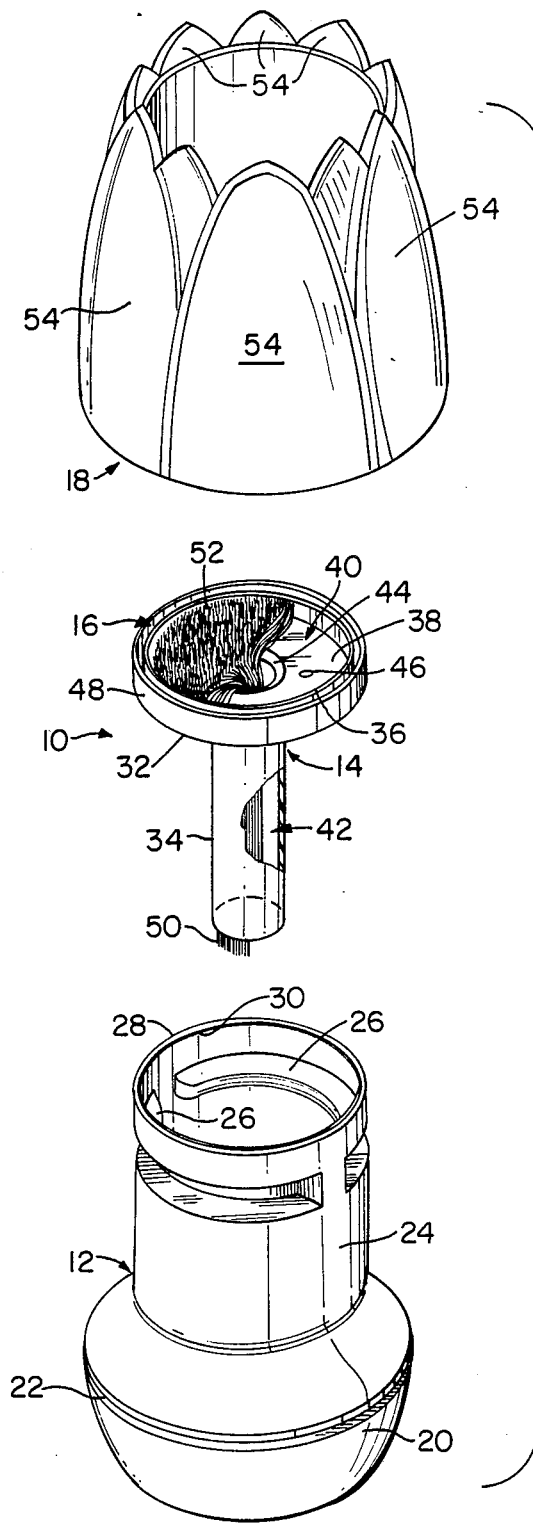
FIG. 1 is an exploded perspective view of an air freshener constructed in accordance with one exemplary embodiment of the present invention.

Referring to FIG. 1, an air freshener 10 includes the following basic components: a base 12, a wick holder 14, a wick 16 and a shroud 18. Set forth below is a more detailed description of these components.

Figure 2:
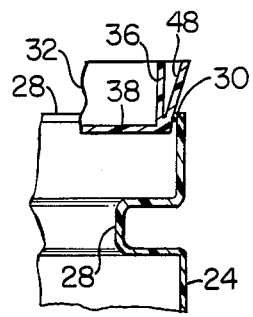
FIG. 2 is a partial cross-sectional view of two elements of the air freshener illustrated in FIG. 1, the two elements being shown in a pre-assembled position.
Figure 3:
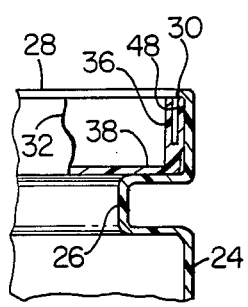
FIG. 3 is a partial cross-sectional view which is similar to FIG. 2, except that the two elements are shown in an assembled position.

The base 12, which is molded monolithically out of a suitable plastic material such as polyethylene, includes a reservoir 20 adapted to receive a predetermined quantity of a conventional scent-producing liquid (not shown). The reservoir 20, which is preferably translucent so that the level of the scent-producing liquid contained therein can be visually observed, has a circular groove 22 for a purpose to be described below. A neck 24 extends upwardly from the reservoir 20. The neck 24 includes inwardly projecting shoulders 26 which function to support the wick holder 14 in a manner to be described hereinafter. The neck 24 also includes an upper rim 28 which is provided with an inwardly projecting circular flange 30 (see FIGS. 2 and 3) adapted to perform a function that will be described below.

The wick holder 14, which is also molded monolithically out of a suitable plastic material such as polypropylene, includes a pan 32 and a stem 34. The pan 32 has a circular sidewall 36 and a flat bottom 38 which cooperates with the sidewall 36 to define an interior chamber 40. The stem 34 has a conduit 42 which communicates with the interior chamber 40 of the pan 32. A chamfered surface 44 is provided at the junction of the conduit 42 and the interior chamber 40 for a purpose to be described hereinafter. A vent hole 46 is provided in the bottom 38 of the pan 32 in order to perform a function that will be described below. The sidewall 36 of the pan 32 includes an upwardly extending, circumferentially continuous skirt 48 which functions like a spring for a purpose to be described hereinafter.

The wick 16 is made from strands of polyester or any other suitable material capable of conveying the scent-producing liquid from the reservoir 20 of the base 12 by way of capillary action. A lower end 50 of the wick 16 extends through the conduit 42 provided in the stem 34 of the wick holder 14, the diameter of the conduit 42 being selected such that the stem 34 maintains the lower end 50 of the wick 16 in a tight bundle to promote the desired capillary action. The wick 16 also includes an upper end 52 which is received in the interior chamber 40 of the pan 32. The upper end 52 of the wick 16 is flared so as to increase its surface area and thereby promote the diffusion of the scent-producing liquid being conveyed by the wick 16. The upper end 52 of the wick 16 is also matted to maintain the proper capillary action.

Figure 4:
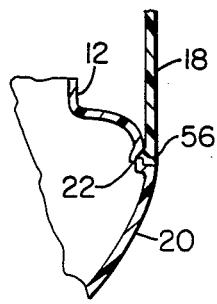
FIG. 4 is a partial cross-sectional view of two elements of the air freshener illustrated in FIG. 1, the two elements being shown in an assembled position.
Figure 5:
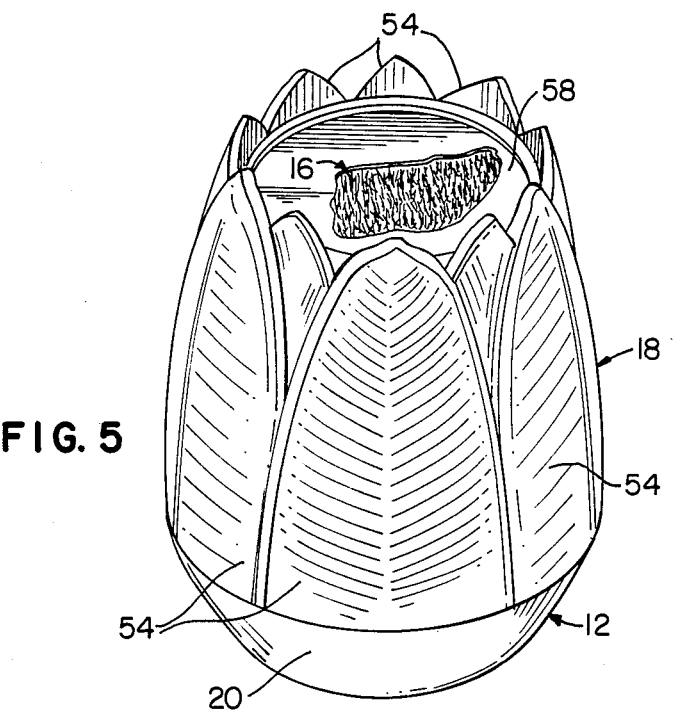
FIG. 5 is a perspective view showing the air freshener of FIG. 1 fully assembled, a portion of the air freshener being broken away to facilitate consideration and discussion.

The shroud 18 has simulated petals 54 so that the air freshener 10, in its assembled state illustrated in FIG. 5, resembles a flower. The shroud 18 also includes an inwardly extending circular bead 56 adapted to be snapped into the groove 22 of the base 12 (see FIG. 4) during the assembly of the air freshener 10.

To assemble the air freshener 10, the reservoir 20 of the base 12 is filled with the scent-producing liquid. Before or after such a filling operation, the wick 16 is inserted into the wick holder 14, the insertion of the wick 16 being facilitated by the chamfered surface 44 which also facilitates the flaring of the upper end 52 of the wick 16. Once the wick 16 has been inserted into the wick holder 14, the wick holder 14 is inserted into the neck 24 of the base 12 until the bottom 38 of the pan 32 rests on the shoulders 26 extending inwardly from the neck 24. As the wick holder 14 is being inserted into the neck 24 of the base 12, the skirt 48 is deflected inwardly (i.e., compressed) by the flange 30 provided on the rim 28 of the neck 24. When the wick holder 14 has been completely inserted into the neck 24 of the base 12, the skirt 48, due to its spring-like construction and the elastic memory of the material from which it is made, is constantly and automatically urged against the neck 24 so as to form a substantially liquid-tight, internal seal which inhibits leakage of the scent-producing liquid contained within the reservoir 20 of the base 12, the formation of such a seal being facilitated by the flange 30. The skirt 48 and the flange 30 also cooperate with each other to lock the wick holder 14 in place. With the wick holder 14 in place, the shroud 18 is pushed onto the base 12 until the bead 56 snaps into the groove 22 to form a snap fit between the base 12 and the shroud 18. The final step of the assembly process involves heat sealing an aluminum poly-coated cover 58 (see FIG. 5) to the upper rim 28 of the neck 24 of the base 12, the cover 58 functioning to control the diffusion of the scent-producing liquid in a manner to be described hereinafter.

When the cover 58 is in place, the diffusion of the scent-producing liquid is prevented. In order to place the air freshener 10 in operation, the cover 58 is removed by a user, whereby the scent-producing liquid contained on the upper end 52 of the wick 16 is exposed to the surrounding atmosphere to thereby cause the diffusion of the scent-producing liquid by the process of evaporation. Thus, with the cover 58 removed, the upper end 52 of the wick 14 forms an external surface of the air freshener 10 and functions as a liquid-diffusing site. As the scent-producing liquid diffuses into the surrounding atmosphere, the diffused liquid is replaced by additional liquid conveyed from the reservoir 20 to the upper end 52 of the wick 14 by capillary action. As the level of the scent-producing liquid in the reservoir 20 decreases, the vacated space in the reservoir 20 is filled with air which enters the base 12 through the vent hole 46 formed in the wick holder 14.

After the scent-producing liquid has been completely used up (a condition which can be observed through the translucent reservoir 20), the wick holder 14 and the wick 16 may be removed from the air freshener 10. With the wick holder 14 and the wick 16 removed, the base 12 may be filled with potting soil and, in combination with the shroud 18, used as a planter.

Because the air freshener 10 is hand sized, it is extremely portable. Thus, the air freshener 10 can be conveniently stored, shipped and displayed. The compact size of the air freshener 10 also allows it to be placed in small areas, such as on countertops and windowsills, and to be moved from room to room.

It will be understood that the embodiment described herein is merely exemplary and that a person skilled in the art may make many variations and modifications without departing from the spirit and scope of the invention. All such variations and modifications are intended to be included within the scope of the invention as defined in the appended claims.

We claim:

1. An air freshener, comprising a base having an open end, an closed end, and receiving means located between said open end and said closed end for receiving a scent-producing liquid; conveying means for conveying the scent-producing liquid from said receiving means to a liquid-diffusing site located in said open end of said base such that the scent-producing liquid can be evaporatively diffused into the atmosphere surrounding said liquid-diffusing site, said conveying means including a wick-like member made from numerous strands of material capable of conveying the scent-producing liquid along said wick-like member from a first end located in said receiving means to a second end located at said liquid-diffusing site by capillary action, each of said strands extending continuously from said receiving means to said liquid-diffusing site such that the scent-producing liquid can be diffused into the surrounding atmosphere directly from said second end of said wick-like member at a relatively constant and uniform rate, said second end of said wick-like member being flared so as to promote the diffusion of the scent-producing liquid and matted so as to maintain the conveyance of the scent-producing liquid by capillary action; a wick holder attached to said base, said wick holder including first holding means for holding said first end of said wick-like member such that said strands of said first end are tightly bundled so as to promote the conveyance of the scent-producing liquid along said wick-like member by capillary action and second holding means for holding said second end of said wick-like member such that said strands of said second end substantially fill said open end of said base, whereby the diffusion of the scent-producing liquid is enhanced as a result of the increased surface area of said second end of said wick-like member, said second holding means including a pan positioned in said open end of said base, said pan having a sidewall and a bottom which cooperate to define an interior chamber sized and shaped so as to receive said second end of said wick-like member, and said first holding means including a stem extending from said bottom of said pan to said receiving means of said base, said stem having a solid outer wall defining a conduit through which said strands of said wick-like member extend from said interior chamber of said pan to said receiving means of said base; supporting means for supporting said wick holder in abutting relationship with said base, whereby an internal joint is formed between said base and said wick holder; and sealing means for sealing said joint in a liquid-tight manner, whereby the inadvertent leakage of the scent-producing liquid from said receiving means is inhibited, said sealing means including a spring-like member having an elasticity selected such that said spring-like member is constantly and automatically urged into intimate contact with said base.

2. An air freshener according to claim 1, wherein said liquid-diffusing site is remote from said receiving means.

3. An air freshener according to claim 2, wherein said liquid-diffusing site is located on an external surface of said air freshener.

4. An air freshener according to claim 1, wherein said strands are made from polyester.

5. An air freshener according to claim 1, further comprising controlling means for controlling the diffusion of the scent-producing liquid from said liquid-diffusing site by controlling the exposure of said liquid-diffusing site to the surrounding atmosphere.

6. An air freshener according to claim 1, wherein said sealing means includes a circumferentially continuous skirt extending outwardly from said sidewall of said pan.

7. An air freshener according to claim 6, wherein said skirt extends upwardly from said sidewall of said pan.

8. An air freshener according to claim 7, wherein said supporting means removably supports said wick holder in said open end of said base, whereby said wick holder and said conveying means can be removed from said base to provide access to said receiving means for the purpose of permitting said base to be filled with potting soil and used as a planter.

9. An air freshener according to claim 8, wherein said base includes a circumscribing groove intermediate said open end and said closed end, said air freshener further comprising a generally truncated domeshaped shroud having a top opening, a bottom opening and a retainer lip disposed about said bottom opening, said retainer lip releasably engaging said groove in said base so as to removably dispose said shroud about an upper portion of said base, said shroud also having a simulated flower petal design thereon, whereby said air freshener resembles a flower.

10. An air freshener according to claim 8, wherein said supporting means includes a circular flange extending radially inward from said open end of said base, said flange releasably engaging said skirt of said sealing means when said skirt is compressed to thereby facilitate the formation of said liquid-tight seal.

11. An air freshener according to claim 9, wherein said base is translucent, whereby the level of the scent-producing liquid can be viewed through said base.

12. An air freshener according to claim 9, wherein said wick holder is removable independently of said shroud, whereby said wick holder and said conveying means can be removed from said base without removing said shroud from said base.

13. An air freshener according to claim 1, wherein said wick holder includes guiding means for guiding said first end of said wick-like member into said conduit of said stem during the insertion of said wick-like member into said wick holder.

14. An air freshener according to claim 13, wherein said guiding means includes a chamfered surface at the interface between said conduit of said stem and said interior chamber of said pan.

15. An air freshener according to claim 14, wherein said bottom of said pan has a vent hole.

* * * * *